(12) United States Patent
Chong et al.

(10) Patent No.: US 8,597,269 B2
(45) Date of Patent: Dec. 3, 2013

(54) RESERVOIR SEAL RETAINER SYSTEMS AND METHODS

(75) Inventors: Colin A. Chong, Burbank, CA (US); Eric M. Lorenzen, Granada Hills, CA (US); Rafael Bikovsky, Oak Park, CA (US); Truong Gia Luan, Winnetka, CA (US); Arsen Ibranyan, Glendale, CA (US); Christopher G. Griffin, Sylmar, CA (US); Philip J. Hudak, Thousand Oaks, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1037 days.

(21) Appl. No.: 12/345,362

(22) Filed: Dec. 29, 2008

(65) Prior Publication Data

US 2009/0259209 A1    Oct. 15, 2009

Related U.S. Application Data

(60) Provisional application No. 61/044,322, filed on Apr. 11, 2008.

(51) Int. Cl.
*A61B 19/00*    (2006.01)
(52) U.S. Cl.
USPC .......................................................... 604/403
(58) Field of Classification Search
USPC .................. 604/200–206, 239–244, 403–416
See application file for complete search history.

(56) References Cited

U.S. PATENT DOCUMENTS

| | | | |
|---|---|---|---|
| 1,712,070 A | 5/1929 | Cressler | |
| 4,465,200 A * | 8/1984 | Percarpio | 215/247 |
| 5,554,134 A * | 9/1996 | Bonnichsen | 604/240 |
| 6,017,331 A * | 1/2000 | Watts et al. | 604/232 |
| 6,088,608 A | 7/2000 | Schulman et al. | |
| 6,119,028 A | 9/2000 | Schulman et al. | |
| 6,589,229 B1 | 7/2003 | Connelly et al. | |
| 6,740,072 B2 | 5/2004 | Starkweather et al. | |
| 6,827,702 B2 | 12/2004 | Lebel et al. | |
| 7,318,816 B2 | 1/2008 | Bobroff et al. | |
| 7,323,142 B2 | 1/2008 | Pendo et al. | |

(Continued)

FOREIGN PATENT DOCUMENTS

| WO | WO 01/70307 A1 | 9/2001 |
|---|---|---|
| WO | WO 2004/030716 A2 | 4/2004 |
| WO | WO 2004/030717 A2 | 4/2004 |

OTHER PUBLICATIONS

International Search Report and Written Opinion for PCT/US2009/038180 dated Aug. 19, 2009.

*Primary Examiner* — Philip R Wiest
(74) *Attorney, Agent, or Firm* — Foley & Lardner LLP

(57) ABSTRACT

At least one tab may extend through at least one opening in a retaining member configured to cover at least a portion of a head of a reservoir body and a portion of a septum supported by the head of the reservoir body. A retaining member may be configured to cover at least a portion of a first head of a reservoir body and a portion of a septum supported by the first head of the reservoir body, and the reservoir body may have a second head having at least one tab. A retaining member located in a head of a reservoir body may be for retaining a septum on the head of the reservoir body, and the head of the reservoir body may have at least one tab.

36 Claims, 14 Drawing Sheets

(56) References Cited

U.S. PATENT DOCUMENTS

| | | |
|---|---|---|
| 7,455,663 B2 | 11/2008 | Bikovsky |
| 2001/0041869 A1 | 11/2001 | Causey, III et al. |
| 2002/0022855 A1 | 2/2002 | Bobroff et al. |
| 2003/0078195 A1 | 4/2003 | Kristensen et al. |
| 2003/0212364 A1 | 11/2003 | Mann et al. |
| 2004/0002682 A1 | 1/2004 | Kovelman et al. |
| 2004/0073095 A1 | 4/2004 | Causey, III et al. |
| 2005/0065760 A1 | 3/2005 | Murtfeldt et al. |
| 2006/0253085 A1 | 11/2006 | Geismar et al. |
| 2006/0264894 A1 | 11/2006 | Moberg et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051738 A1 | 2/2008 | Griffin |
| 2008/0051765 A1 | 2/2008 | Mounce |
| 2008/0077081 A1 | 3/2008 | Mounce et al. |
| 2008/0097291 A1 | 4/2008 | Hanson et al. |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |

\* cited by examiner

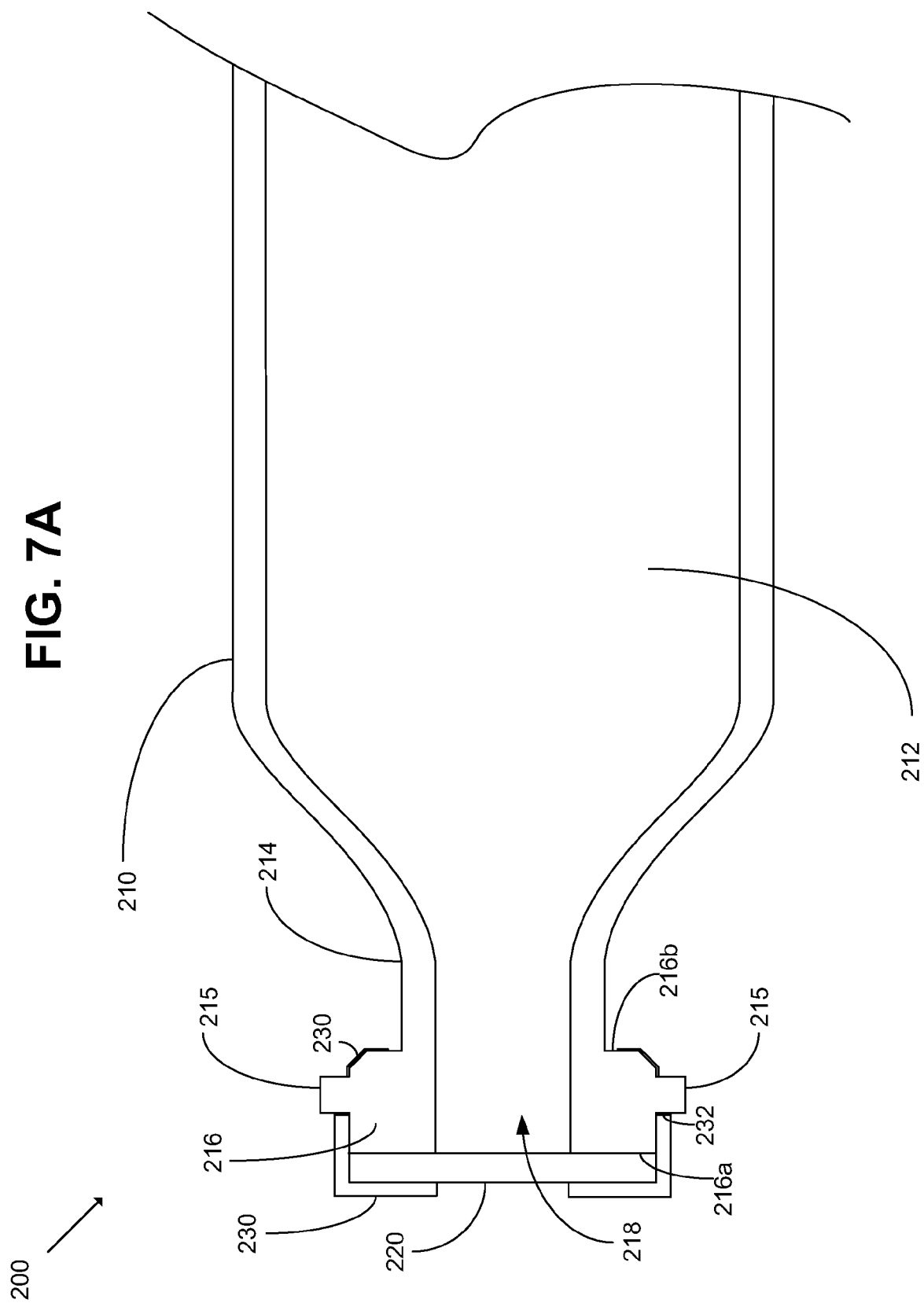

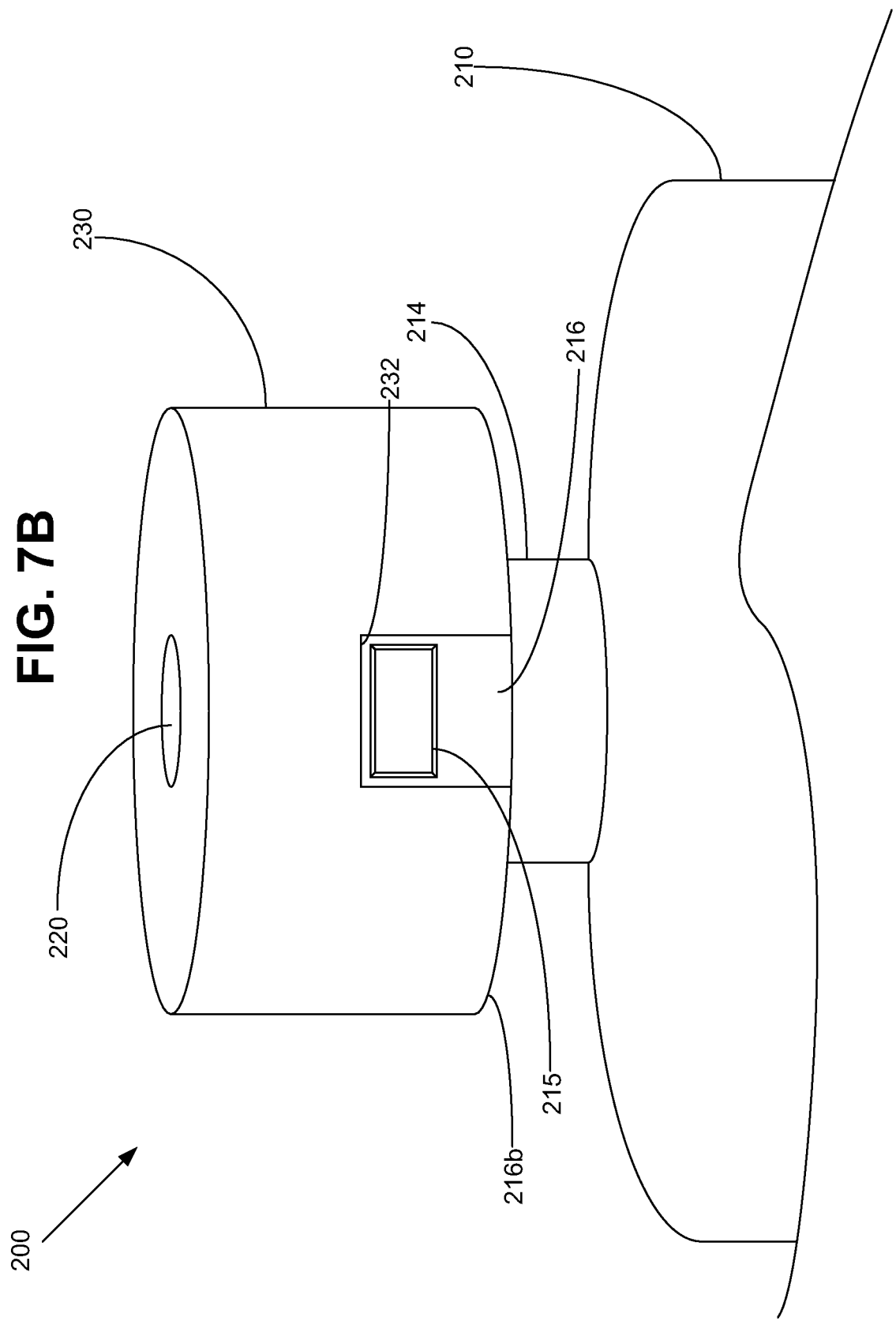

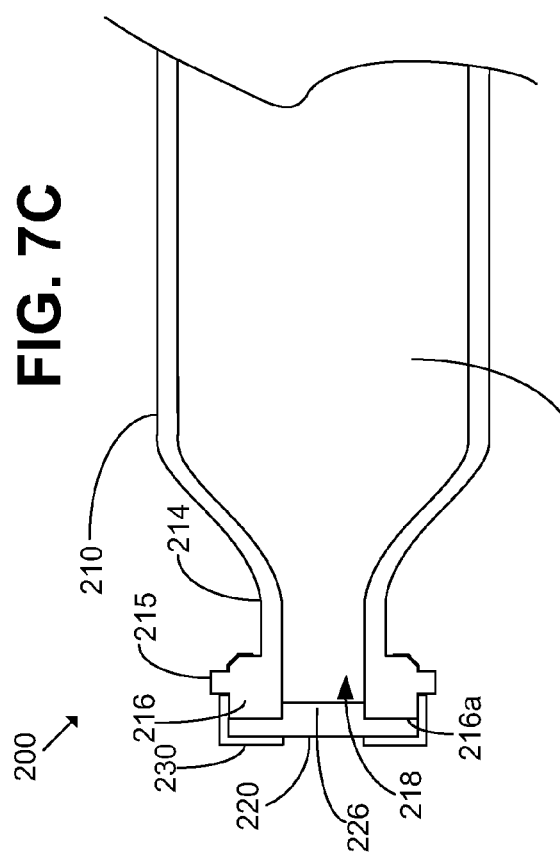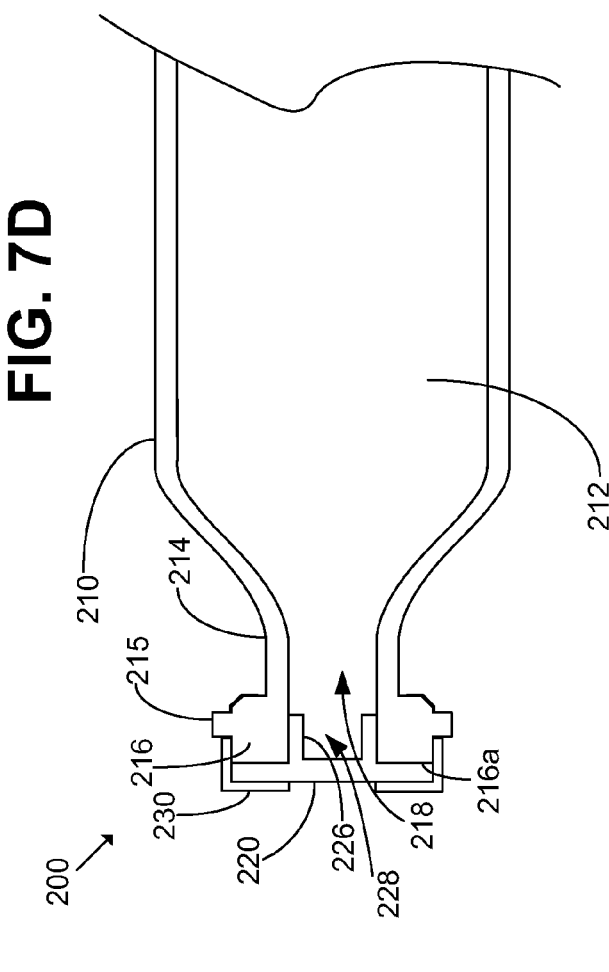

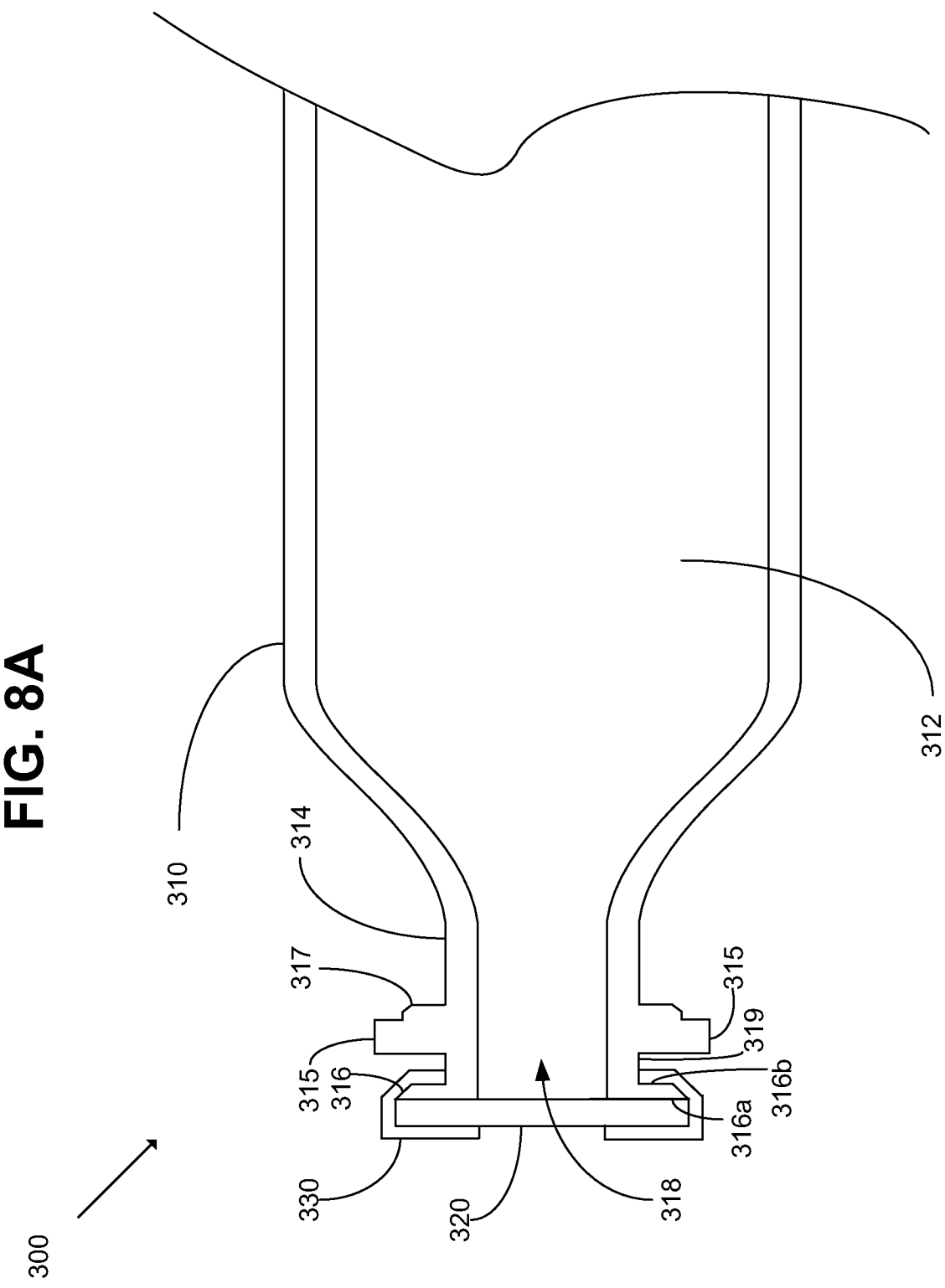

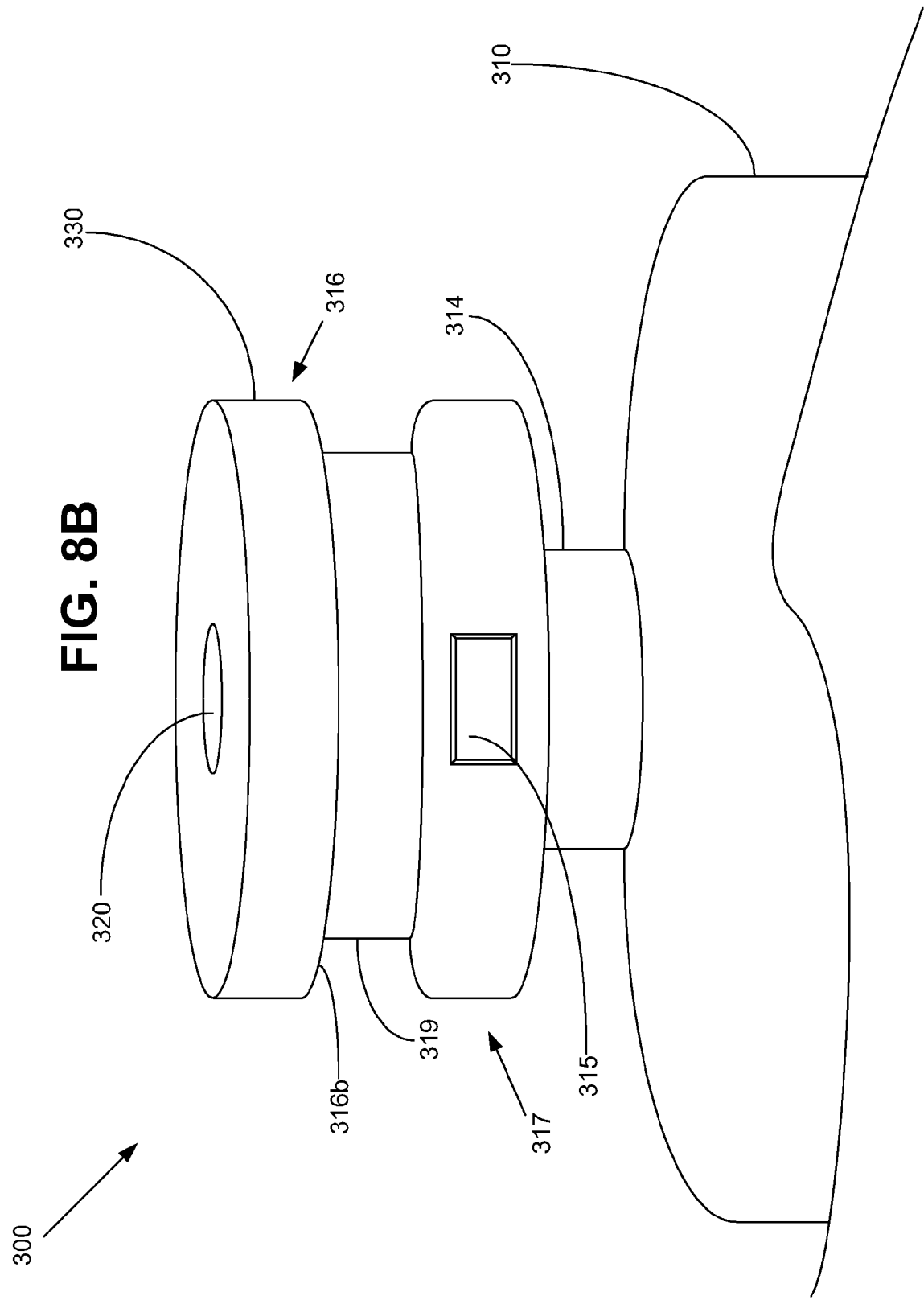

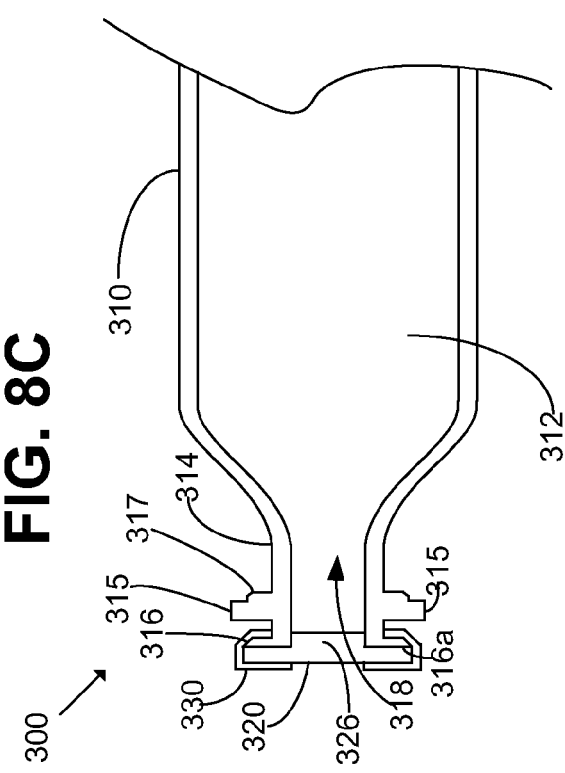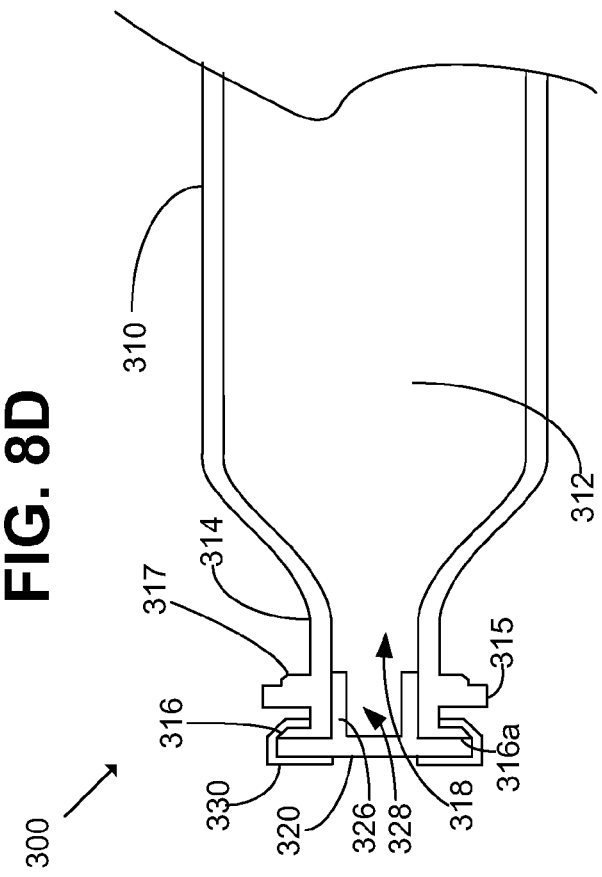

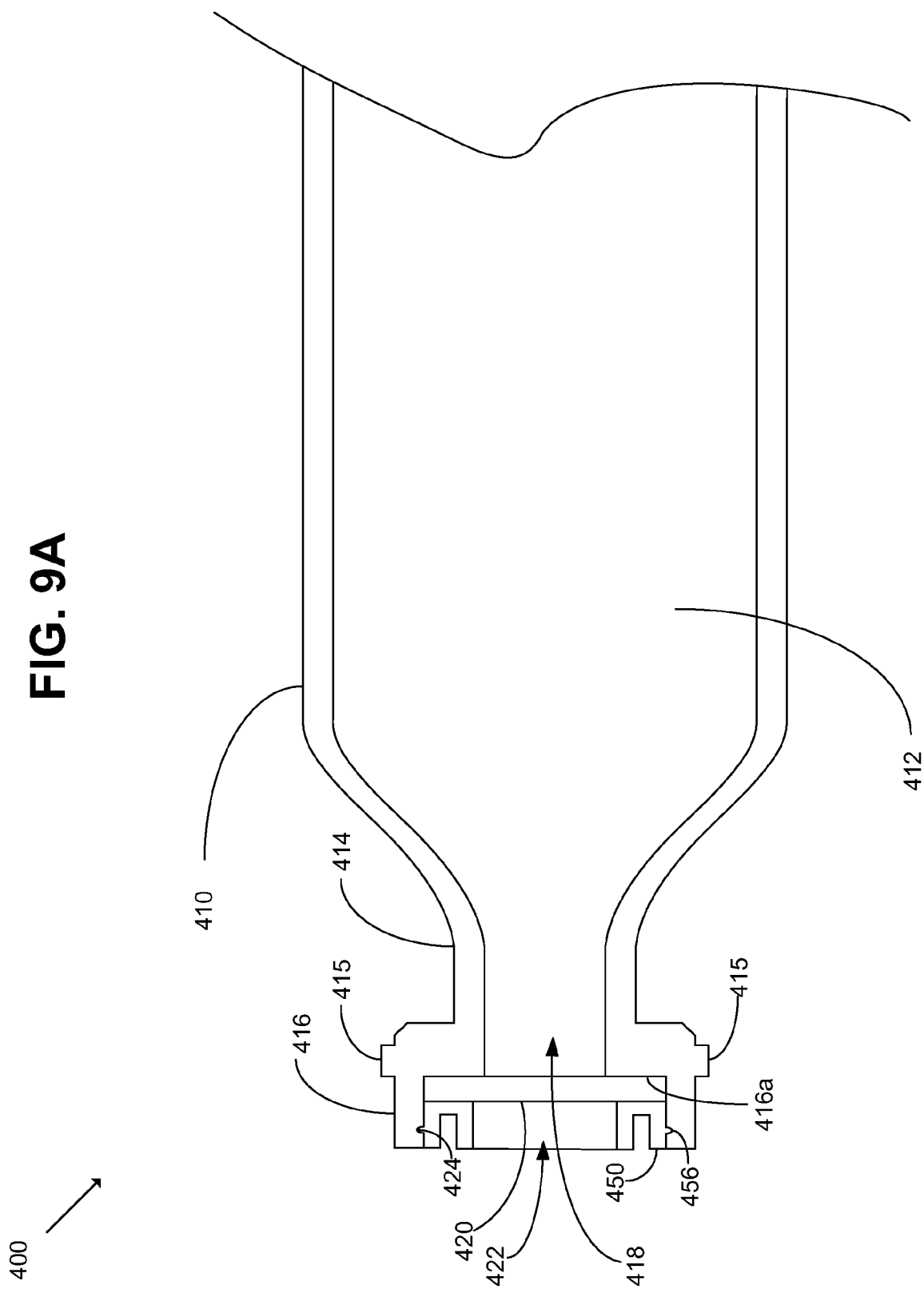

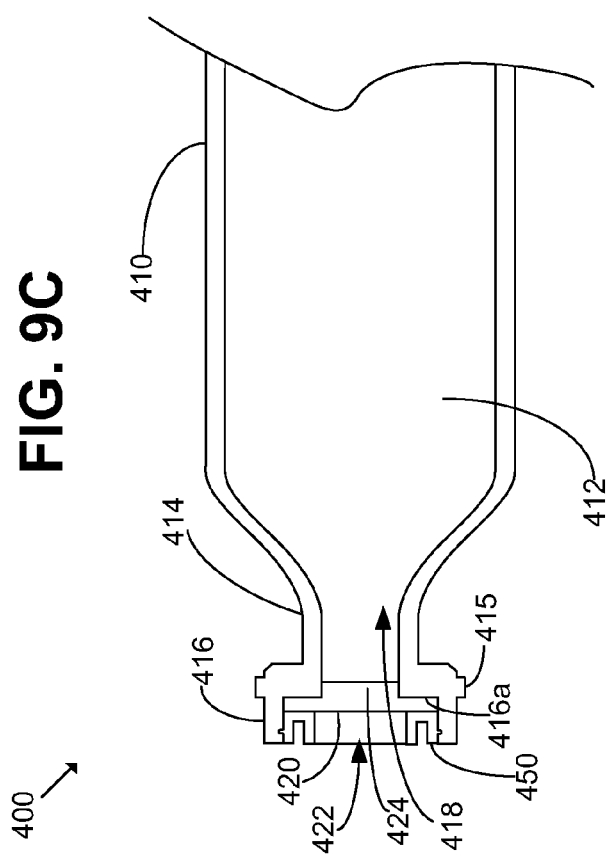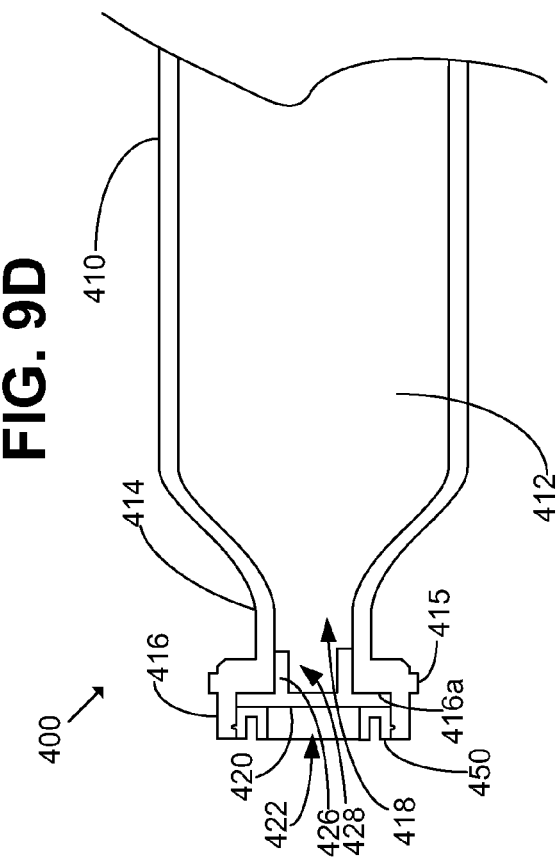

RESERVOIR SEAL RETAINER SYSTEMS AND METHODS

CROSS-REFERENCE TO RELATED PATENT APPLICATIONS

This application claims priority from Provisional U.S. Application 61/044,322, filed Apr. 11, 2008, incorporated herein by reference in its entirety.

BACKGROUND OF THE INVENTION

1. Field of the Invention

Embodiments of the present invention relate generally to reservoir systems and methods and infusion systems and methods having such reservoir systems and methods and, in specific embodiments, to such reservoir systems and methods with retaining seals and components thereof.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump-type delivery devices have been configured in external devices, which connect to a patient, and have also been configured in implantable devices, which are implanted inside of the body of a patient. External pump-type delivery devices include devices designed for use in a stationary location, such as a hospital, a clinic, or the like, and further include devices configured for ambulatory or portable use, such as devices that are designed to be carried by a patient, or the like. External pump-type delivery devices may contain reservoirs of fluidic media, such as, but is not limited to, insulin. External pump-type delivery devices may be connected in fluid flow communication to a patient or user, for example, through a suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a user-patient, for example, through a suitable hollow tubing. The hollow tubing may be connected to a hollow needle that is designed to pierce the user-patient's skin and deliver an infusion medium to the user-patient. Alternatively, the hollow tubing may be connected directly to the user-patient as or through a cannula or set of micro-needles.

In contexts in which the hollow tubing is connected to the user-patient through a hollow needle that pierces the user-patient's skin, a manual insertion of the needle into the user-patient can be somewhat traumatic to the user-patient. Accordingly, insertion mechanisms have been made to assist the insertion of a needle into the user-patient, whereby a needle is forced by a spring to quickly move from a retracted position into an extended position. As the needle is moved into the extended position, the needle is quickly forced through the user-patient's skin in a single, relatively abrupt motion that can be less traumatic to certain user-patients as compared to a slower, manual insertion of a needle. While a quick thrust of the needle into the user-patient's skin may be less traumatic to some patient's than a manual insertion, it is believed that, in some contexts, some patients may feel less trauma if the needle is moved a very slow, steady pace. Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211, 095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

As compared to syringes and insulin pens, pump type delivery devices can be significantly more convenient to a user-patient, in that accurate doses of insulin may be calculated and delivered automatically to a user-patient at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and as doctors and user-patients become more familiar with such devices, the popularity of external medical infusion pump treatment increases and is expected to increase substantially over the next decade.

SUMMARY OF THE DISCLOSURE

A system for transferring fluidic media in accordance with an embodiment of the present invention may include, but is not limited to, a reservoir body, a septum, and a retaining member. The reservoir body may be for containing fluidic media. The reservoir body may have a head and a port located at the head of the reservoir body. The head of the reservoir body may have at least one tab extending from the head of the reservoir body. The septum may be supported by the head of the reservoir body. The septum may be configured to substantially seal the port of the reservoir body. The retaining member may be configured to cover at least a portion of the head of the reservoir body and to cover at least a portion of the septum. The at least one tab may be uncovered by the retaining member when the retaining member covers the at least a portion of the head.

In various embodiments, the retaining member may have at least one opening. The at least one tab may extend through the at least one opening in the retaining member when the retaining member covers the at least a portion of the head.

In various embodiments, the reservoir body may be configured to be removably attachable to a fluid delivery device. In some embodiments, the at least one tab on the head of the reservoir body may be dimensioned and arranged to be insertable into at least one aperture in the fluid delivery device for removably attaching the reservoir body to the fluid delivery device.

In various embodiments, the retaining member may comprise a casing configured to cover and receive at least a portion of the head of the reservoir body and to cover at least a portion of the septum. In various embodiments, the retaining member may be configured to be arranged adjacent no more than three sides of the at least one tab. In various embodiments, the reservoir body may be pre-filled with fluidic media. In various embodiments, the retaining member may comprise a metal material.

In various embodiments, the head may have an upper surface for supporting the septum and a lower surface opposite the upper surface. The retaining member may be configured to cover at least a portion of the lower surface of the head of the reservoir body.

In various embodiments, the reservoir body may have a neck that has a smaller cross-sectional dimension than a remaining portion of the reservoir body. The head of the reservoir body may be located at an end of the neck of the reservoir body.

In various embodiments, the septum may have a portion extending into the port of the reservoir body. In some embodiments, the portion of the septum may have a hollow interior.

In various embodiments, the head may comprise a first head and a second head. The port of the reservoir body may be located at the first head of the reservoir body. The septum may be supported by the first head of the reservoir body. The retaining member may be configured to cover at least a portion of the first head of the reservoir body and to cover at least a portion of the septum. The at least one tab may be located on the second head of the reservoir body.

In some embodiments, the first head may have an upper surface for supporting the septum and a lower surface opposite the upper surface. The retaining member may be configured to cover at least a portion of the lower surface of the first head of the reservoir body.

In some embodiments, the reservoir body may have a neck that has a smaller cross-sectional dimension than a remaining portion of the reservoir body. The second head of the reservoir body may be located on the neck of the reservoir body. The first head of the reservoir body may be located at an end of the neck of the reservoir body.

In some embodiments, the first head of the reservoir body may have a first diameter. The second head of the reservoir body may have a second diameter. The first diameter of the first head may be substantially comparable in size and dimension to the second diameter of the second head. In some embodiments, the at least one tab on the second head of the reservoir body may extend beyond the retaining member when the retaining member covers the at least a portion of the first head of the reservoir body.

In various embodiments, the head of the reservoir body may have a cavity aligned with the port of the reservoir body. The septum may be located in the cavity of the head of the reservoir body. The septum may be supported by a seating surface of the head of the reservoir body.

In some embodiments, the retaining member may be located in the cavity of the head of the reservoir body. The retaining member may be configured to retain the septum on the seating surface of the head of the reservoir body. In further embodiments, the retaining member may be located entirely within the cavity of the head of the reservoir body. In other embodiments, the retaining member may be located substantially within the cavity of the head of the reservoir body. In some embodiments, the septum may be positioned between the retaining member and the seating surface of the head of the reservoir body.

In some embodiments, the cavity of the head of the reservoir body may be defined by an interior sidewall of the head of the reservoir body. The interior sidewall of the head of the reservoir body may have one or more recesses. The retaining member may have one or more retaining tabs insertable into the one or more recesses in the interior sidewall of the head of the reservoir body. The one or more retaining tabs may be for securing the retaining member to the reservoir body.

In some embodiments, the cavity of the head of the reservoir body may be defined by an interior sidewall of the head of the reservoir body. The retaining member may have one or more recesses. The interior sidewall of the head of the reservoir body may have one or more retaining tabs insertable into the one or more recesses in the retaining member. the one or more retaining tabs may be for securing the retaining member to the reservoir body.

A method of making a system for transferring fluidic media may include, but is not limited to, any one of or combination of: (i) providing a reservoir body for containing fluidic media, the reservoir body may have a head and a port located at the head of the reservoir body; (ii) supporting a septum on the head of the reservoir body, the septum may be configured to substantially seal the port of the reservoir body; (iii) providing a retaining member configured to cover at least a portion of the head of the reservoir body and to cover at least a portion of the septum; (iv) extending at least one tab from the head of the reservoir body; and (v) covering at least a portion of the head of the reservoir body with the retaining member, wherein the at least one tab is uncovered by the retaining member.

In various embodiments, the retaining member may have at least one opening. The at least one tab may extend through the at least one opening in the retaining member when the retaining member covers the at least a portion of the head.

In various embodiments, the head may comprise a first head and a second head. The port of the reservoir body may be located at the first head of the reservoir body. The septum may be supported by the first head of the reservoir body. The retaining member may be configured to cover at least a portion of the first head of the reservoir body and to cover at least a portion of the septum. The at least one tab may be located on the second head of the reservoir body.

In various embodiments, providing a retaining member may comprise arranging the retaining member in a cavity in the head of the reservoir body. The cavity may be aligned with the port of the reservoir body. The septum may be located in the cavity of the head of the reservoir body. The septum may be supported by a seating surface of the head of the reservoir body. The retaining member may be configured to retain the septum on the seating surface of the head of the reservoir body.

BRIEF DESCRIPTION OF THE DRAWINGS

FIG. 7A illustrates a cross-section of a system for transferring fluidic media in accordance with an embodiment of the present invention;

FIG. 7B illustrates a side view of a system for transferring fluidic media in accordance with an embodiment of the present invention;

FIG. 7C illustrates a cross-section of a system for transferring fluidic media in accordance with an embodiment of the present invention;

FIG. 7D illustrates a cross-section of a system for transferring fluidic media in accordance with an embodiment of the present invention;

FIG. 8A illustrates a cross-section of a system for transferring fluidic media in accordance with an embodiment of the present invention;

FIG. 8B illustrates a side view of a system for transferring fluidic media in accordance with an embodiment of the present invention;

FIG. 8C illustrates a cross-section of a system for transferring fluidic media in accordance with an embodiment of the present invention;

FIG. 8D illustrates a cross-section of a system for transferring fluidic media in accordance with an embodiment of the present invention;

FIG. 9A illustrates a cross-section of a system for transferring fluidic media in accordance with an embodiment of the present invention;

FIG. 9C illustrates a cross-section of a system for transferring fluidic media in accordance with an embodiment of the present invention; and FIG. 9D illustrates a cross-section of a system for transferring fluidic media in accordance with an embodiment of the present invention.

DETAILED DESCRIPTION OF THE PREFERRED EMBODIMENTS

Figure 1:
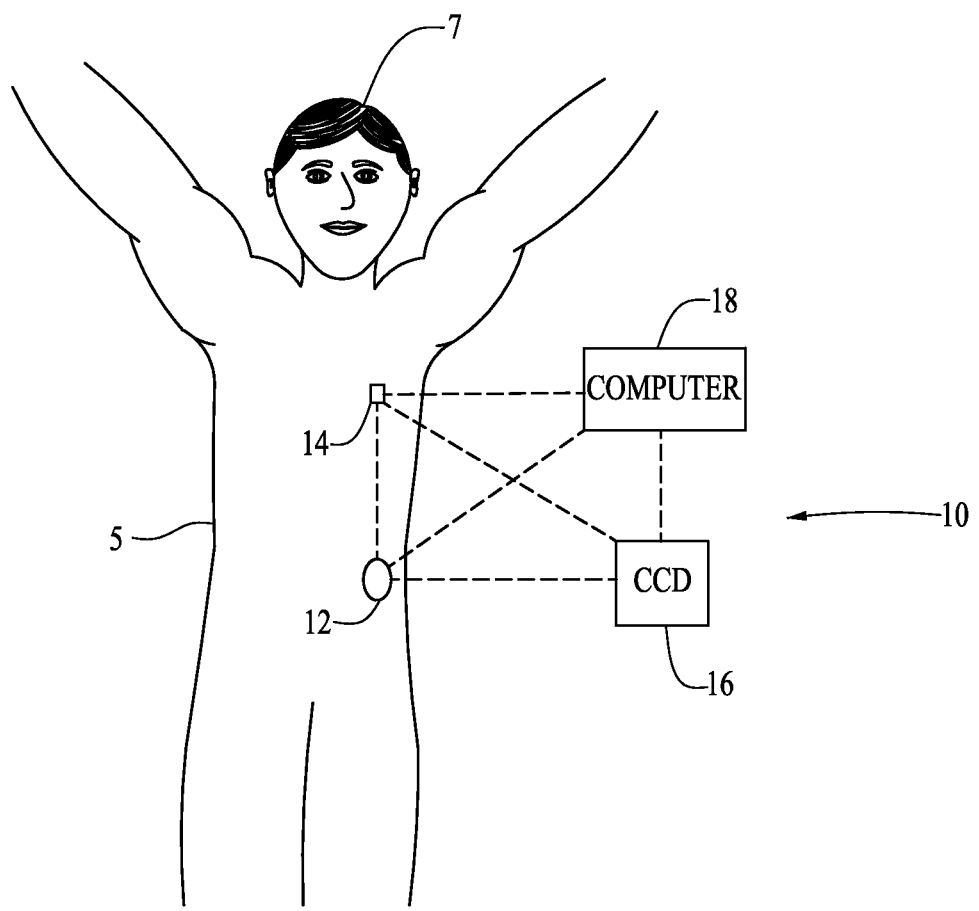
FIG. 1 illustrates a generalized representation of a system in accordance with an embodiment of the present invention.

FIG. 1 illustrates a generalized representation of a system 10 in accordance with an embodiment of the present invention. The system 10 includes a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, delivery device 12, sensing device 14, CCD 16 and computer 18 may be similar to those described in the following U.S. patent applications that were assigned to the assignee of the present invention, however, with a reservoir and plunger configuration such as described herein with reference to FIGS. 7-8C, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; and (xix) U.S. patent application Ser. No. 11/759,725, filed Jun. 7, 2007, "Infusion Medium Delivery Device And Method With Drive Device For Driving Plunger In Reservoir". In other embodiments, the system 10, delivery device 12, sensing device 14, CCD 16, and computer 18 may have other suitable configurations.

The delivery device 12 is configured to deliver fluidic media to the body 5 of the user-patient 7. In various embodiments, fluidic media includes a liquid, a fluid, a gel, or the like. In some embodiments, fluidic media includes a medicine or a drug for treating a disease or a medical condition. For example, fluidic media may include insulin for treating diabetes, or may include a drug for treating pain, cancer, a pulmonary disorder, HIV, or the like. In some embodiments, fluidic media includes a nutritional supplement, a dye, a tracing medium, a saline medium, a hydration medium, or the like.

The sensing device 14 includes a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7. In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In other embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. Also, in various embodiments, the delivery device 12 and/or the sensing device 14 may be configured to transmit data to the CCD 16 and/or the computer 18 for display or processing of the data by the CCD 16 and/or the computer 18.

Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same", all of which are incorporated herein by reference in their entirety.

Figure 2:
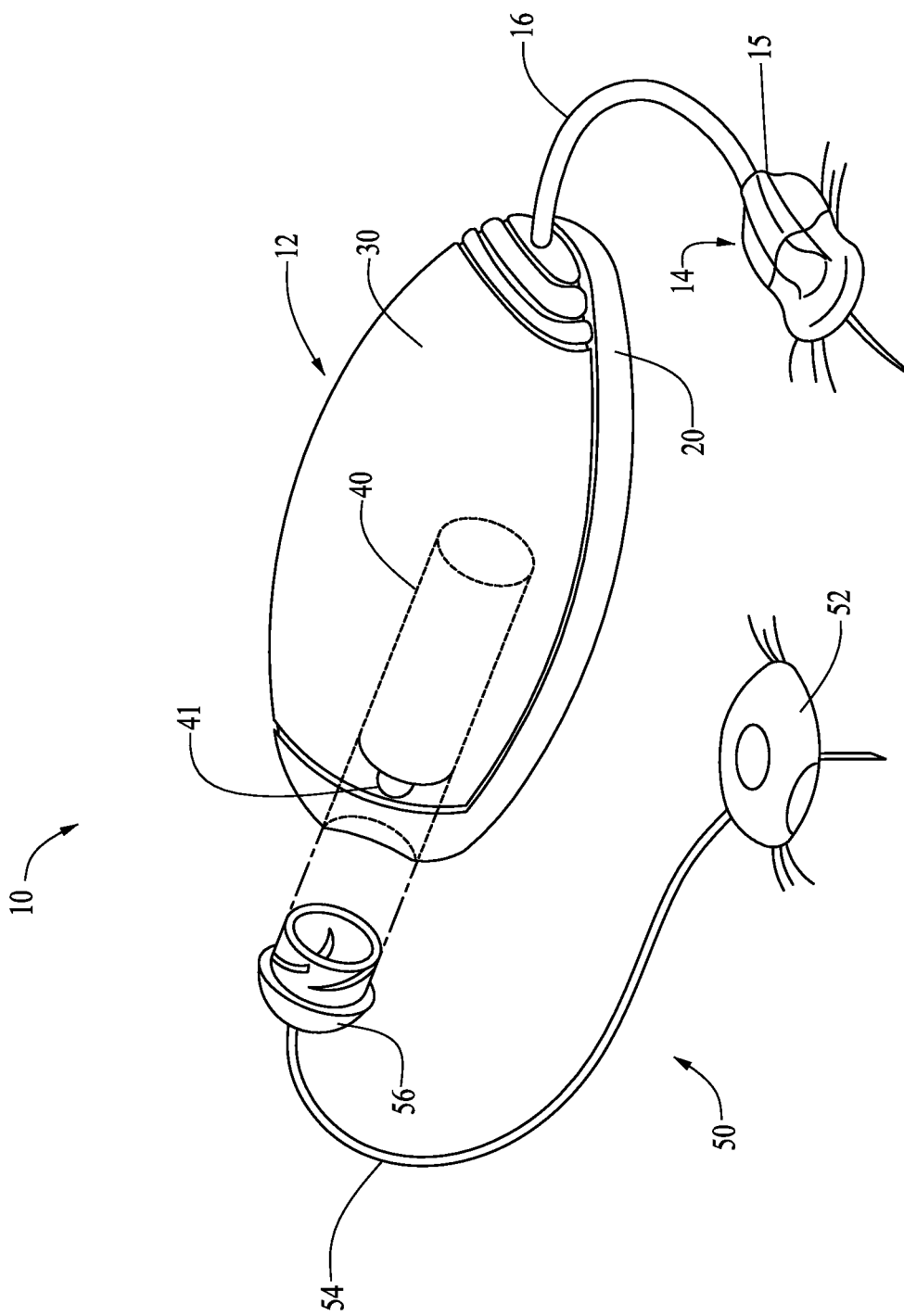
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 supports the reservoir system 40 and has a bottom surface (facing downward and into the page in FIG. 2) that is configured to secure to the body of a user-patient. An adhesive may be employed at an interface between the bottom surface of the disposable housing 20 and the skin of a user-patient, so as to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12 may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 is configured for containing or holding fluidic media, such as, but not limited to insulin. In various embodiments, the reservoir system 40 includes a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 is able to be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 includes a port 41 for allowing fluidic media to flow into and/or flow out of the interior volume of the reservoir system 40. In some embodiments, the infusion path 50 includes a connector 56, a tube 54, and a needle apparatus 52. The connector 56 of the infusion path 50 may be connectable to the port 41 of the reservoir system 40. In various embodiments, the disposable housing 20 is configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 is covered with or supports a septum (not shown in FIG. 2), such as a self-sealing septum, or the like. The septum may be configured to prevent fluidic media from flowing out of the reservoir system 40 through the port 41 when the septum is not pierced. Also, in various embodiments, the connector 56 of the infusion path 50 includes a needle for piercing the septum covering the port 41 of the reservoir system 40 so as to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector", which is incorporated herein by reference in its entirety. In other alternatives, non-septum connectors such as Luer locks, or the like may be used. In various embodiments, the needle apparatus 52 of the infusion path 50 includes a needle that is able to puncture the skin of a user-patient. Also, in various embodiments, the tube 54 connects the connector 56 with the needle apparatus 52 and is hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20, so as to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction so as to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same", which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. Also, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 16 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set", which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 includes a sensor 15 connected by the connection element 16 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
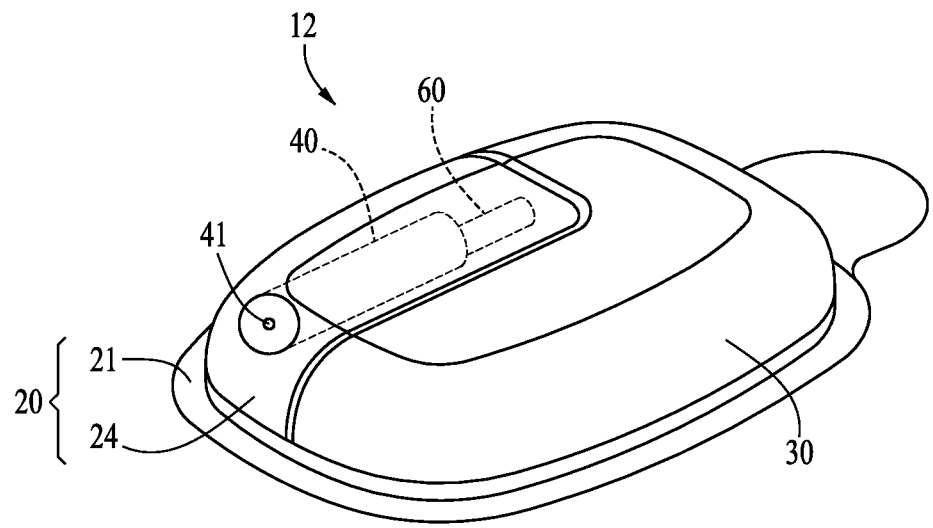
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 is configured to be secured to the body of a user-patient. The reservoir retaining portion 24 of the disposable housing 20 is configured to house the reservoir system 40. The reservoir retaining portion 24 of the disposable housing 20 may be configured to have an opening to allow for the port 41 of the reservoir system 40 to be accessed from outside of the reservoir retaining portion 24 while the reservoir system 40 is housed in the reservoir retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
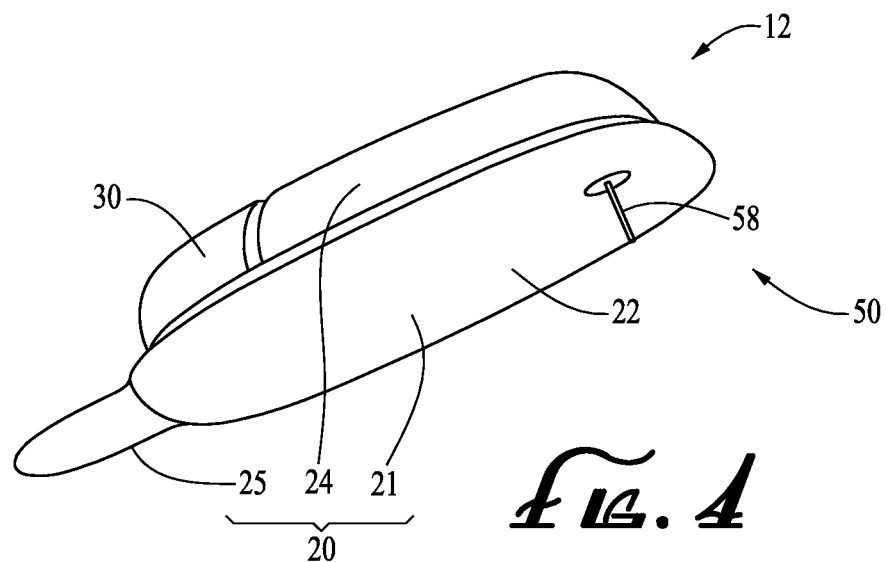
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
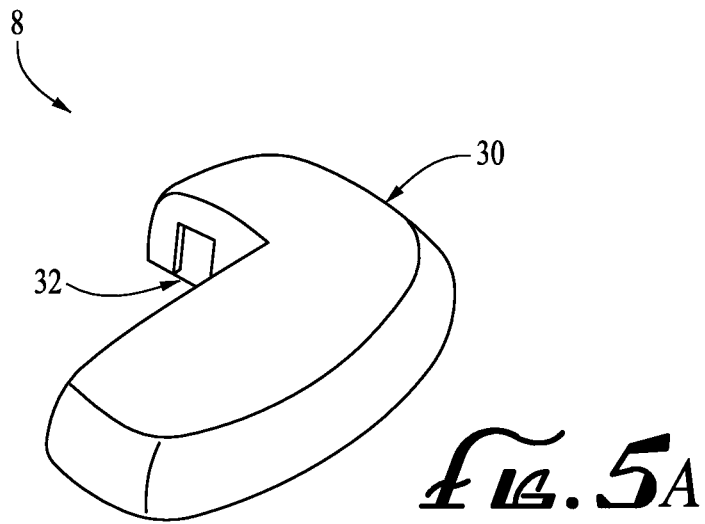
FIG. 5A illustrates a durable portion of a delivery device in accordance with an embodiment of the present invention.
Figure 5B:
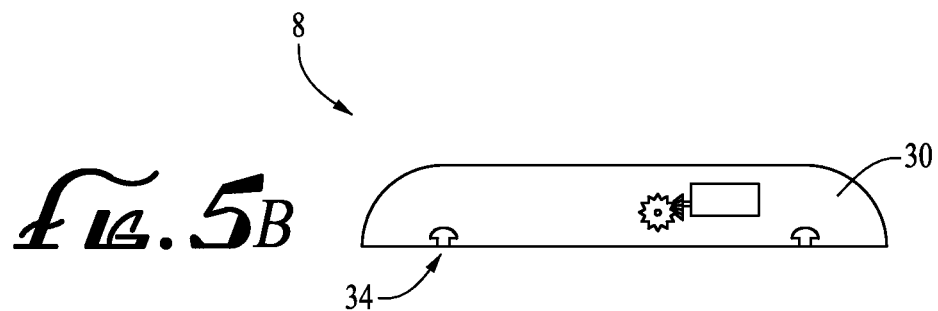
FIG. 5B illustrates a section view of a durable portion of a delivery device in accordance with an embodiment of the present invention.
Figure 5C:
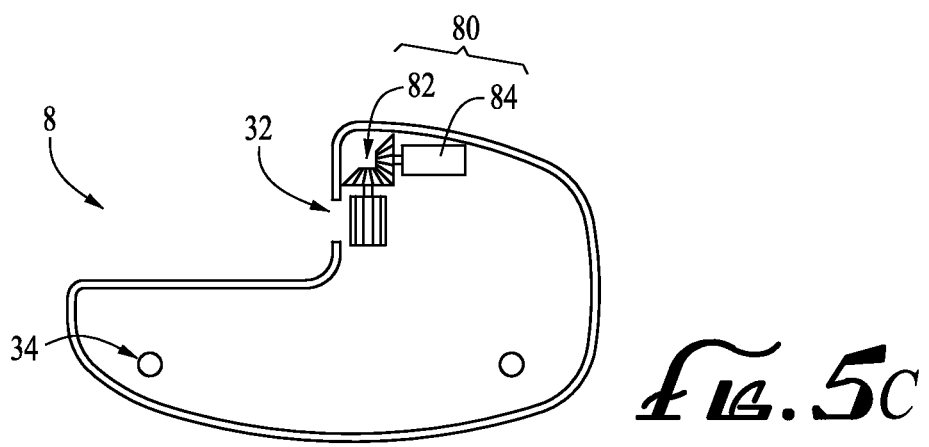
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). Also, in various embodiments, the durable housing 30 is configured with an opening 32 for receiving a plunger arm 60 (refer to FIG. 3). Also, in various embodiments, the durable housing 30 may include one or more connection members 34, such as tabs, insertion holes, or the like, for connecting with the base 21 of the disposable housing 20 (refer to FIG. 3).

Figure 6A:
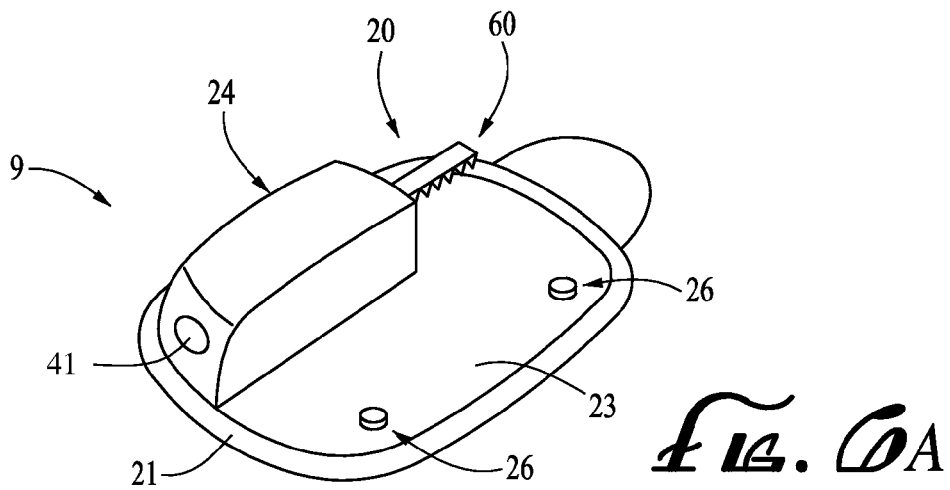
FIG. 6A illustrates a disposable portion of a delivery device in accordance with an embodiment of the present invention.
Figure 6B:
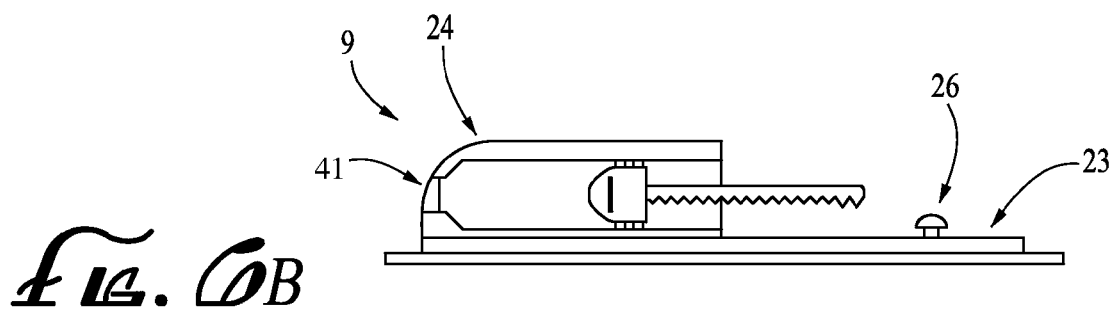
FIG. 6B illustrates a section view of a disposable portion of a delivery device in accordance with an embodiment of the present invention.
Figure 6C:
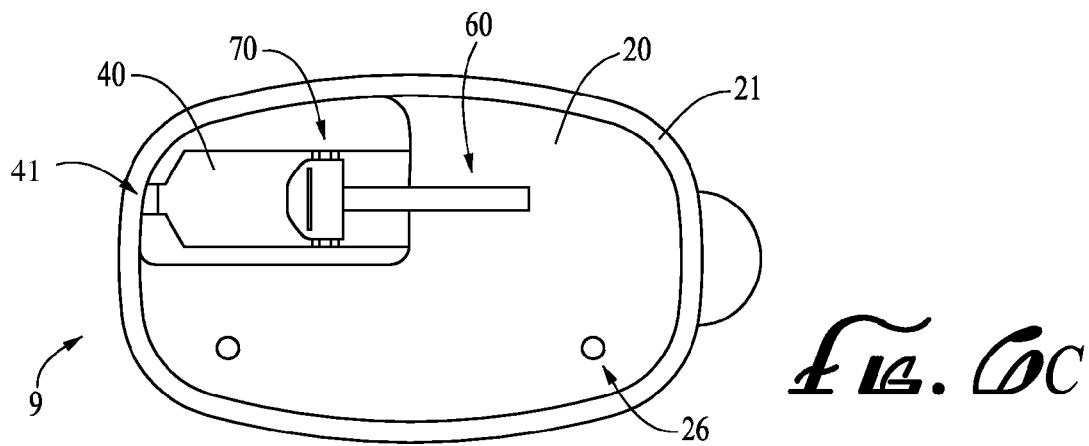
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 includes the base 21 and the reservoir retaining portion 24. In various embodiments, the base 21 includes a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 is housed within the reservoir retaining portion 24 of the disposable housing 20, and the reservoir system 40 is configured to hold fluidic media. Also, in various embodiments, the plunger head 70 is disposed at least partially within the reservoir system 40 and is moveable within the reservoir system 40 to allow fluidic media to fill into the reservoir system 40 and to force fluidic media out of the reservoir system 40. In some embodiments, the plunger arm 60 is connected to or is connectable to the plunger head 70.

Also, in some embodiments, a portion of the plunger arm 60 extends to outside of the reservoir retaining portion 24 of the disposable housing 20. In various embodiments, the plunger arm 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, a user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. Also, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 includes reservoir status circuitry (not shown), and the reservoir system 40 includes reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 includes the reservoir status circuitry (not shown), and the reservoir status circuitry is configured to read data from the reservoir circuitry when the reservoir system 40 is inserted into the disposable portion 9.

In various embodiments, the reservoir status circuitry is further configured to store data to the reservoir circuitry after at least some of the contents of the reservoir system 40 have been transferred out of the reservoir system 40, so as to update information in the reservoir circuitry related to an amount of contents still remaining in the reservoir system 40. In some embodiments, the reservoir status circuitry is configured to store data to the reservoir circuitry, so as to update information in the reservoir circuitry related to an amount of contents still remaining in the reservoir system 40, when the reservoir system 40 is inserted into the disposable portion 9. In some embodiments, the delivery device 12 includes the reservoir status circuitry (not shown) and the reservoir system 40 includes the reservoir circuitry (not shown), and the reservoir status circuitry selectively inhibits use of the delivery device 12 or selectively provides a warning signal based on information read by the reservoir status circuitry from the reservoir circuitry.

FIGS. 7A and 7B illustrate a reservoir system 200 that may be employed as an embodiment of the reservoir system 40 discussed above, for delivering fluidic media in accordance with an embodiment of the present invention. The reservoir system 200 may include, but is not limited to, a reservoir 210, a septum 220, and a retaining member 230. The reservoir 210 may have an interior volume 212 for containing fluidic media. The reservoir 210 may have a port 218 for expelling or receiving fluidic media contained in the interior volume 212 of the reservoir 210. In various embodiments, the reservoir 210 may be made of various suitable materials, including, but not limited to, glass, plastic, TOPAS® polymers, or the like.

The reservoir 210 may have a neck portion 214 that tapers around the port 218 of the reservoir 210. The neck portion 214 may have a cross-sectional dimension less than a remaining portion of the reservoir 210. The reservoir 210 may have a head portion 216 located near an end of the neck portion 214 of the reservoir 210. The head portion 216 of the reservoir 210 may surround the port 218 of the reservoir 210.

The septum 220 may be supported on a stop surface 216a of the head portion 216 of the reservoir 210 to substantially cover or otherwise seal the port 218 of the reservoir 210. The septum 220 may be pierceable by a needle (not shown) to allow fluidic media to flow into or out the port 218 of the reservoir 210 and through the needle (not shown). In some embodiments, such as the embodiment illustrated in FIG. 7C, a portion 226 of the septum 220 may extend into the port 218 of the reservoir 210. In further embodiments, such as the embodiment illustrated in FIG. 7D, the portion 226 of the septum 220 that extends into the port 218 of the reservoir 210 may have a hollow interior 228.

Returning to FIGS. 7A and 7B, the retaining member 230 may be a casing or the like. The retaining member 230 may be located around the head portion 216 of the reservoir 210. The retaining member 230 may be configured to substantially cover or surround the head portion 216 of the reservoir 210 and at least a portion of the septum 220. The retaining member 230 may be configured to retain the septum 220 on head portion 216 of the reservoir 210. In various embodiments, the retaining member 230 may be made of any suitable material, such as a metal, (e.g., aluminum), or the like. The retaining member 230 may be for retaining the septum 220 in place over the port 218 of the reservoir 210 to substantially seal the port 218 of the reservoir 210.

The reservoir 210 may be configured to be removably attachable to a delivery device (not shown), an example of which is illustrated in FIG. 2 where the reservoir system 40 is connectable to the connector 56 of the delivery device 10. Returning to FIGS. 7A and 7B, the head portion 216 of the reservoir 210 may be configured to be insertable within the delivery device (not shown) to attach the reservoir 210 to the delivery device (not shown). The reservoir 210 may include at least one tab 215 located around a diameter of the head portion 216 of the reservoir 210. The at least one tab 215 on the head portion 216 may be for attaching the reservoir 210 to the delivery device (not shown).

For example, the at least one tab 215 on the head portion 216 may be dimensioned and arranged to be insertable into one or more recesses (not shown), apertures, or the like in the delivery device (not shown). The at least one tab 215 on the head portion 216 of the reservoir 210 may be inserted within the one or more recesses (not shown) of the delivery device (not shown), then the reservoir 210 may be, for example, rotated to lock or otherwise attach the reservoir 210 to the delivery device (not shown).

In some embodiments, the retaining member 230 may substantially cover or surround the head portion 216 of the reservoir 210. In some embodiments, the retaining member 230 may be configured to cover at least a portion of a bottom surface 216b of the head portion 216 of the reservoir 210. The bottom surface 216b of the head portion 216 of the reservoir 210 may be opposite the top surface 216a, which may be supporting the septum 220, of the head portion 216 of the reservoir 210.

In some embodiments, the retaining member 230 may include at least one opening or slot 232 (refer to FIG. 7B) through which the at least one tab 215 on the head portion 216 of the reservoir 210 may extend. The at least one slot 232 in the retaining member 230 may allow for sufficient clearance to allow the at least one tab 215 to extend beyond the retaining member 230. In some embodiments, the retaining member 230 may be configured to be arranged adjacent at most three sides of the at least one tab 215 on the head portion 216 of the reservoir 210. Thus, in various embodiments, the at least one tab 215 may be uncovered by the retaining member 230 covering at least a portion of the head portion 216 of the reservoir 210.

In various embodiments, the reservoir 210 may be pre-filled with fluidic media prior to the reservoir 210 being used by a user-patient. In some embodiments, the reservoir 210 may be filled with fluidic media before the septum 220 and/or the retaining member 230 are/is placed on the head portion 216 of the reservoir 210 to substantially seal the port 218 of the reservoir 210.

In various embodiments where the reservoir 210 is pre-filled with fluidic media, the reservoir 210 may include a plunger head (not shown) that may be attachable to the delivery device (not shown). In further embodiments, the plunger head (not shown) may be placed in the reservoir 210 before or after the reservoir 210 is filled with fluidic media. The plunger head (not shown) may be made of Bromobutyl rubber, silicone rubber, or any other suitable material and/or any derivative thereof.

FIGS. 8A and 8B illustrate a reservoir system 300 that may be employed as an embodiment of the reservoir system 40 discussed above, for delivering fluidic media in accordance with an embodiment of the present invention. The reservoir system 300 may include, but is not limited to, a reservoir 310, a septum 320, and a retaining member 330. The reservoir 310 may have an interior volume 312 for containing fluidic media. The reservoir 310 may have a port 318 for expelling or receiving fluidic media contained in the interior volume 312 of the reservoir 310. In various embodiments, the reservoir 310 may be made of various suitable materials, including, but not limited to, glass, plastic, TOPAS® polymers, or the like.

The reservoir 310 may have a neck portion 314 that tapers around the port 318 of the reservoir 310. The neck portion 314 may have a cross-sectional dimension less than a remaining portion of the reservoir 310. The reservoir 310 may have a first head portion 316 and a second head portion 317 located on the neck portion 314 of the reservoir 310. The first head portion 316 may be located near an end of the neck portion 314 of the reservoir 310. The first head portion 316 of the reservoir 310 may surround the port 318 of the reservoir 310. The first head portion 316 and the second head portion 317 of the reservoir may taper to a mid-portion 319.

The septum 320 may be supported on a top surface 316a of the first head portion 316 of the reservoir 310 to substantially cover or otherwise seal the port 318 of the reservoir 310. The septum 320 may be pierceable by a needle (not shown) to allow fluidic media to flow into or out the port 318 of the reservoir 310 and through the needle (not shown). In some embodiments, such as the embodiment illustrated in FIG. 8C, a portion 326 of the septum 320 may extend into the port 318 of the reservoir 310. In further embodiments, such as the embodiment illustrated in FIG. 8D, the portion 326 of the septum 320 that extends into the port 318 of the reservoir 310 may have a hollow interior 328.

Returning to FIGS. 8A and 8B, the retaining member 330 may be a casing or the like. The retaining member 330 may be located around the first head portion 316 of the reservoir 310. The retaining member 330 may be configured to substantially cover or surround the first head portion 316 of the reservoir 310 and at least a portion of the septum 320. The retaining member 330 may be configured to retain the septum 320 on the first head portion 316 of the reservoir 310. In various embodiments, the retaining member 330 may be made of any suitable material, such as a metal, (e.g., aluminum), or the like. The retaining member 330 may be for retaining the septum 320 in place over the port 318 of the reservoir 310 to substantially seal the port 318 of the reservoir 310.

In some embodiments, the retaining member 330 may substantially cover or surround the first head portion 316 of the reservoir 310. In some embodiments, the retaining member 330 may be configured to cover at least a portion of a bottom surface 316b of the first head portion 316 of the reservoir 310. The bottom surface 316b of the first head portion 316 of the reservoir 310 may be opposite the top surface 316a, which may be supporting the septum 320, of the first head portion 316 of the reservoir 310.

In various embodiments, the first head portion 316 of the reservoir 310 may have a diameter that is of comparable size and dimension to a diameter of the second head portion 317 of the reservoir 310. In various embodiments, because the retaining member 330 covers at least a portion of the first head portion 316 and the at least one tab 315 is located on the second head portion 317, the at least one tab 315 may be uncovered by the retaining member 330.

The reservoir 310 may be configured to be removably attachable to a delivery device (not shown), an example of which is illustrated in FIG. 2 where the reservoir system 40 is connectable to the connector 56 of the delivery device 10. Returning to FIGS. 8A and 8B, the first head portion 316 and the second head portion 317 of the reservoir 310 may be configured to be insertable within the delivery device (not shown) to attach the reservoir 310 to the delivery device (not shown). The reservoir 310 may include at least one tab 315 located around the diameter of the second head portion 317 of the reservoir 310. Because the diameter of the first head portion 316 of the reservoir 310 may be of comparable size and dimension to the diameter of the second head portion 317 of the reservoir 310, the at least one tab 315 located around the diameter of the second head portion 317 may extend beyond the first head portion 316 of the reservoir 310.

The at least one tab 315 on the second head portion 317 of the reservoir 310 may be for attaching the reservoir 310 to the delivery device (not shown). For example, the at least one tab 315 on the second head portion 317 may be dimensioned and arranged to be insertable into one or more recesses (not shown), apertures, or the like in the delivery device (not shown). The at least one tab 315 on the second head portion 317 of the reservoir 310 may be inserted within the one or more recesses (not shown) of the delivery device (not shown), then the reservoir 310 may be rotated to lock or otherwise attach the reservoir 310 to the delivery device (not shown).

In various embodiments, the reservoir 310 may be pre-filled with fluidic media prior to the reservoir 310 being used by a user-patient. In some embodiments, the reservoir 310 may be filled with fluidic media before the septum 320 and/or the retaining member 330 are/is placed on the first head portion 316 of the reservoir 310 to substantially seal the port 318 of the reservoir 310.

In various embodiments where the reservoir 310 is pre-filled with fluidic media, the reservoir 310 may include a plunger head (not shown) that may be attachable to the delivery device (not shown). In further embodiments, the plunger head (not shown) may be placed in the reservoir 310 before or after the reservoir 310 is filled with fluidic media. The plunger head (not shown) may be made of Bromobutyl rubber, silicone rubber, or any other suitable material and/or any derivative thereof.

Figure 9B:
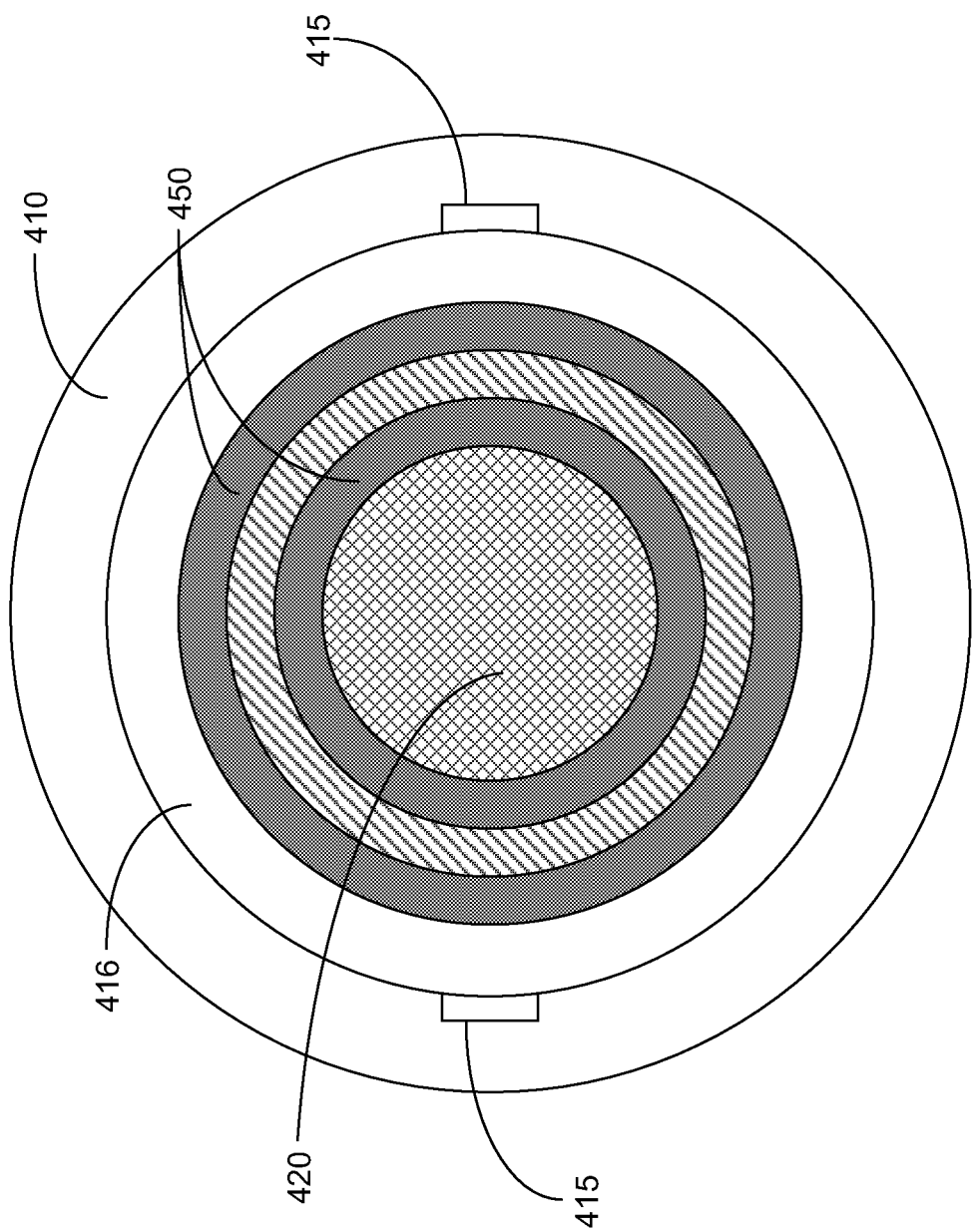
FIG. 9B illustrates a top-down view of a system for transferring fluidic media in accordance with an embodiment of the present invention.

FIGS. 9A and 9B illustrate a reservoir system 400 that may be employed as an embodiment of the reservoir system 40 discussed above, for delivering fluidic media in accordance with an embodiment of the present invention. The reservoir system 400 may include, but is not limited to, a reservoir 410, a septum 420, and a retaining member 450. The reservoir 410 may have an interior volume 412 for containing fluidic media. The reservoir 410 may have a port 418 for expelling or receiving fluidic media contained in the interior volume 412 of the reservoir 410. In various embodiments, the reservoir 410 may be made of various suitable materials, including, but not limited to, glass, plastic, TOPAS® polymers, or the like.

The reservoir 410 may have a neck portion 414 that tapers around the port 418 of the reservoir 410. The neck portion 414 may have a cross-sectional dimension less than a remaining portion of the reservoir 410. The reservoir 410 may have a head portion 416 located on the neck portion 414 of the reservoir 410. The head portion 416 may be located near an end of the neck portion 414 of the reservoir 410. The head portion 416 of the reservoir 410 may surround the port 418 of the reservoir 410.

The head portion 416 may have a cavity 422 formed within. The cavity 422 in the head portion 416 may be aligned with the port 418 of the reservoir 410. The septum 420 may be located in the cavity 422 in the head portion 416 and may be supported on a seating surface 416a of the head portion 416 of the reservoir 410 to substantially cover or otherwise seal the port 418 of the reservoir 410. The septum 420 may be pierceable by a needle (not shown) to allow fluidic media to flow into or out the port 418 of the reservoir 410 and through the needle (not shown). In some embodiments, such as the embodiment illustrated in FIG. 9C, a portion 426 of the septum 420 may extend into the port 418 of the reservoir 410. In further embodiments, such as the embodiment illustrated in FIG. 9D, the portion 426 of the septum 420 that extends into the port 418 of the reservoir 410 may have a hollow interior 428.

Returning to FIGS. 9A and 9B, the retaining member 450 may be located in the cavity 422 in the head portion 416 and may be supported above the septum 420 that is supported on the seating surface 416a of the head portion 416 of the reservoir 410. The retaining member 450 may cover at least a portion (e.g., interior sidewall) of the head portion 416 of the reservoir 410 and/or the septum 420. The retaining member 450 may be for retaining the septum 420 in place over the port 418 of the reservoir 410 to substantially seal the port 418 of the reservoir 410. The retaining member 450 may be made of any suitable material, such as a metal, (e.g., aluminum), or the like.

In some embodiments, the retaining member 450 may be press-fit into the cavity 422 of the head portion 416 of the reservoir 410. In other embodiments, the retaining member 450 may be placed or fit into the cavity 422 in any suitable manner to retain the septum 420 in place over the port 418 of the reservoir 410. For example, in some embodiments, the retaining member 450 may be adapted to be insertable, arrangeable, and/or removable with a tool (not shown). The tool (not shown) may be adapted to connect, attach, or otherwise fit to the retaining member 450. For example, the retaining member 450 may have a recess 458 for receiving the tool (not shown). The tool (not shown) may be fit within the recess 458 to support the retaining member 450 in inserting, removing, and/or arranging the retaining member 450 in the cavity 422. In further embodiments, the tool (not shown) and/or the retaining member 450 may be configured to lock the retaining member 450 to the reservoir body 410. For example, the retaining member 450 may include tabs and/or recesses that complement recesses and/or tabs in the reservoir, and can engage one and other, for example, through rotation the retaining member 450.

In some embodiments, the retaining member 450 may have at least one retaining tab 456 insertable into one or more recesses 424 formed on an interior sidewall of the head portion 416 that defines the cavity 422 in the head portion 416 of the reservoir 410. The at least one retaining tab 456 may be for retaining or otherwise securing the retaining member 450 to the reservoir 410 when the at least one retaining tab 456 is inserted into the one or more recesses 424 formed on the interior sidewall of the head portion 416 of the reservoir 410. In other embodiments, one or more retaining tabs may be located on the interior sidewall of the head portion 416, and the retaining member 450 may include one or more recesses for receiving the one or more retaining tabs.

The reservoir 410 may be configured to be removably attachable to a delivery device (not shown), an example of which is illustrated in FIG. 2 where the reservoir system 40 is connectable to the connector 56 of the delivery device 10. Returning to FIGS. 9A and 9B, the head portion 416 of the reservoir 410 may be configured to be insertable within the delivery device (not shown) to attach the reservoir 410 to the delivery device (not shown). The reservoir 410 may include at least one tab 415 located around a diameter of the head portion 416 of the reservoir 410. The at least one tab 415 on the head portion 416 may be for attaching the reservoir 410 to the delivery device (not shown).

For example, the at least one tab 415 on the head portion 416 may be dimensioned and arranged to be insertable into one or more recesses (not shown), apertures, or the like in the delivery device (not shown). The at least one tab 415 on the head portion 416 of the reservoir 410 may be inserted within the one or more recesses (not shown) of the delivery device (not shown), then the reservoir 410 may be rotated to lock or otherwise attach the reservoir 410 to the delivery device (not shown).

In various embodiments, the reservoir 410 may be prefilled with fluidic media prior to the reservoir 410 being used by a user-patient. In some embodiments, the reservoir 410 may be filled with fluidic media before the septum 420 and/or the retaining member 450 are/is placed in the cavity 422 in the head portion 416 of the reservoir 410 to substantially seal the port 418 of the reservoir 410.

In various embodiments where the reservoir 410 is prefilled with fluidic media, the reservoir 410 may include a plunger head (not shown) that may be attachable to the delivery device (not shown). In further embodiments, the plunger head (not shown) may be placed in the reservoir 410 before or after the reservoir 410 is filled with fluidic media. The plunger head (not shown) may be made of Bromobutyl rubber, silicone rubber, or any other suitable material and/or any derivative thereof.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A reservoir system for containing a fluidic media, the system comprising:
   a reservoir body for containing fluidic media, the reservoir body having a first body section, a head located at one end of the first body section, a port located at the head of the reservoir body, and at least one tab extending from the head of the reservoir body;
   a septum supported by the head of the reservoir body, the septum configured to substantially seal the port of the reservoir body; and
   a retaining member configured to cover at least a portion of the head of the reservoir body and to cover at least a portion of the septum;
   wherein the at least one tab is uncovered by the retaining member when the retaining member covers the at least a portion of the head;
   wherein the reservoir body has a longitudinal axis such that the head of the reservoir body and the first body section of the reservoir body are arranged along the longitudinal axis;
   wherein the at least one tab has an exposed surface for attaching the reservoir body to a delivery device, the exposed surface facing away from the head and transverse to the longitudinal axis of the reservoir body; and
   wherein the exposed surface of the at least one tab is located between the first body section of the reservoir body and the septum in a direction of the longitudinal axis.

2. The system of claim 1, the retaining member having at least one opening, the at least one tab extending through the at least one opening in the retaining member when the retaining member covers the at least a portion of the head.

3. The system of claim 2,
wherein a portion of each tab is removably attachable to a fluid delivery device; and
wherein the portion of each tab that is removably attachable to the fluid delivery device is aligned with the opening.

4. The system of claim 1, the reservoir body configured to be removably attachable to a fluid delivery device.

5. The system of claim 4, the at least one tab on the head of the reservoir body dimensioned and arranged to be insertable into at least one aperture in the fluid delivery device for removably attaching the reservoir body to the fluid delivery device.

6. The system of claim 4,
wherein the at least one tab comprises of a plurality of tabs;
wherein the exposed surface of each of the plurality of tabs is supported to engage the fluid delivery device.

7. The system of claim 1, the retaining member comprising a casing having an interior volume configured to receive at least a portion of the head of the reservoir body.

8. The system of claim 1, the retaining member configured to be arranged adjacent no more than three sides of the at least one tab.

9. The system of claim 1, wherein the reservoir body is pre-filled with fluidic media.

10. The system of claim 1, wherein the retaining member comprises a metal material.

11. The system of claim 1, the head having an upper surface for supporting the septum and a lower surface opposite the upper surface, the retaining member configured to cover at least a portion of the lower surface of the head of the reservoir body.

12. The system of claim 1, wherein the reservoir body having a neck that has a smaller cross-sectional dimension than a cross-sectional dimension of the remaining portion of the reservoir body, the head of the reservoir body located at an end of the neck of the reservoir body.

13. The system of claim 1, the septum having a portion extending into the port of the reservoir body.

14. The system of claim 12, the portion of the septum having a hollow interior.

15. The system of claim 1,
the head comprising a first head and a second head, the port of the reservoir body located at the first head of the reservoir body;
the septum supported by the first head of the reservoir body;
the retaining member configured to cover at least a portion of the first head of the reservoir body and to cover at least a portion of the septum; and
the at least one tab located on the second head of the reservoir body.

16. The system of claim 15, the first head having an upper surface for supporting the septum and a lower surface opposite the upper surface, the retaining member configured to cover at least a portion of the lower surface of the first head of the reservoir body.

17. The system of claim 15, the reservoir body having a neck that has a smaller cross-sectional dimension than a remaining portion of the reservoir body, the second head of the reservoir body located on the neck of the reservoir body, the first head of the reservoir body located at an end of the neck of the reservoir body.

18. The system of claim 15,
the first head of the reservoir body having a first diameter;
the second head of the reservoir body having a second diameter;
wherein the first diameter of the first head is substantially comparable in size and dimension to the second diameter of the second head.

19. The system of claim 15, wherein the at least one tab on the second head of the reservoir body extends beyond the retaining member when the retaining member covers the at least a portion of the first head of the reservoir body.

20. The system of claim 1,
the head of the reservoir body having a cavity aligned with the port of the reservoir body; and
the septum located in the cavity of the head of the reservoir body, the septum supported by a seating surface of the head of the reservoir body.

21. The system of claim 20, the retaining member located in the cavity of the head of the reservoir body, the retaining member configured to retain the septum on the seating surface of the head of the reservoir body.

22. The system of claim 21, wherein the retaining member is located entirely within the cavity of the head of the reservoir body.

23. The system of claim 21, wherein the retaining member is located substantially within the cavity of the head of the reservoir body.

24. The system of claim 21, wherein the septum is positioned between the retaining member and the seating surface of the head of the reservoir body.

25. The system of claim 21,
the cavity of the head of the reservoir body defined by an interior sidewall of the head of the reservoir body;
the interior sidewall of the head of the reservoir body having one or more recesses;
the retaining member having one or more retaining tabs insertable into the one or more recesses in the interior sidewall of the head of the reservoir body, the one or more retaining tabs for securing the retaining member to the reservoir body.

26. The system of claim 21,
the cavity of the head of the reservoir body defined by an interior sidewall of the head of the reservoir body;
the retaining member having one or more recesses;
the interior sidewall of the head of the reservoir body having one or more retaining tabs insertable into the one or more recesses in the retaining member, the one or more retaining tabs for securing the retaining member to the reservoir body.

27. The system of claim 1, wherein the entire exposed surface of each tab is located between the entire septum and the first body section of the reservoir body.

28. The system of claim 1,
wherein the at least one tab includes a first tab and a second tab; and
wherein the exposed surface of the first tab is separate and apart from the exposed surface of the second tab.

29. The system of claim 1,
wherein the at least one tab extends linearly outward in no more than one direction from the head of the reservoir body, in a direction which transverses the longitudinal axis.

30. A method of making a system for transferring fluidic media, the method comprising:
providing a reservoir body for containing fluidic media, the reservoir body having a head, a first body section, and a port located at the head of the reservoir body, the head of the reservoir body is located at an end of the first body section, wherein the head of the reservoir body and the first body section are arranged along a longitudinal axis;

supporting a septum on the head of the reservoir body, the septum configured to substantially seal the port of the reservoir body;

providing a retaining member configured to cover at least a portion of the head of the reservoir body and to cover at least a portion of the septum;

extending at least one tab from the head of the reservoir body, the at least one tab having an exposed surface for attaching the reservoir body to a delivery device, the exposed surface facing in a direction away from the head and transverse to the longitudinal axis of the reservoir body;

covering at least a portion of the head of the reservoir body with the retaining member, wherein at least a part of the at least one tab is uncovered by the retaining member; and arranging the exposed surface of the at least one tab so that the exposed surface of the at least one tab is between the first body section of the reservoir body and the septum in a direction of the longitudinal axis.

31. The method of claim 30, the retaining member having at least one opening, the at least one tab extending through the at least one opening in the retaining member when the retaining member covers the at least a portion of the head.

32. The method of claim 30, the head comprising a first head and a second head, the port of the reservoir body located at the first head of the reservoir body;

the septum supported by the first head of the reservoir body;

the retaining member configured to cover at least a portion of the first head of the reservoir body and to cover at least a portion of the septum; and the at least one tab located on the second head of the reservoir body.

33. The method of claim 30, wherein providing a retaining member comprises arranging the retaining member in a cavity in the head of the reservoir body, the cavity aligned with the port of the reservoir body, the septum located in the cavity of the head of the reservoir body, the septum supported by a seating surface of the head of the reservoir body, the retaining member configured to retain the septum on the seating surface of the head of the reservoir body.

34. A reservoir system, for containing a fluidic media, the system comprising:

a reservoir body for containing fluidic media, the reservoir body having a first body section, a head located at one end of the first body section, and a port located at the head of the reservoir body, the head of the reservoir body having a plurality of tabs extending from the head of the reservoir body, the plurality of tabs including a first tab and a second tab;

a septum supported by the head of the reservoir body, the septum configured to substantially seal the port of the reservoir body; and a retaining member configured to cover at least a portion of the head of the reservoir body and to cover at least a portion of the septum;

wherein each tab is uncovered by the retaining member when the retaining member covers the at least a portion of the head;

wherein the reservoir body has a longitudinal axis such that the head of the reservoir body and the first body section of the reservoir body are arranged along the longitudinal axis;

wherein each tab has an end having an exposed surface;

wherein the exposed surface of each tab is located between the first body section of the reservoir body and the septum in a direction of the longitudinal axis;

wherein the exposed surface of the first tab is separate and apart from the exposed surface of the second tab; and wherein the exposed surface of each of the first tab and the second tab faces away from an interior volume of the reservoir.

35. A reservoir system, for containing a fluidic media, the system comprising:

a reservoir body for containing fluidic media, the reservoir body having a first body section, a head located at one end of the first body section, and a port located at the head of the reservoir body, the head of the reservoir body having at least one tab extending from the head of the reservoir body;

a septum supported by the head of the reservoir body, the septum configured to substantially seal the port of the reservoir body; and a retaining member configured to cover at least a portion of the head of the reservoir body and to cover at least a portion of the septum;

wherein the at least one tab is uncovered by the retaining member when the retaining member covers the at least a portion of the head;

wherein the reservoir body has a longitudinal axis such that the head of the reservoir body and the first body section of the reservoir body are arranged along the longitudinal axis;

wherein the at least one tab has an end with an exposed surface;

wherein the exposed surface of the at least one tab is located between the first body section of the reservoir body and the septum in a direction of the longitudinal axis;

wherein the exposed surface of the at least one tab faces away from an interior volume of the reservoir body.

36. A reservoir system, for containing a fluidic media, the system comprising:

a reservoir body for containing fluidic media, the reservoir body having a first body section, a head located at one end of the first body section, and a port located at the head of the reservoir body, the head of the reservoir body having at least one tab extending from the head of the reservoir body;

a septum supported by the head of the reservoir body, the septum configured to substantially seal the port of the reservoir body; and a retaining member configured to cover at least a portion of the head of the reservoir body and to cover at least a portion of the septum;

wherein the at least one tab is uncovered by the retaining member when the retaining member covers the at least a portion of the head;

wherein the reservoir body has a longitudinal axis such that the head of the reservoir body and the first body section of the reservoir body are arranged along the longitudinal axis;

wherein the at least one tab has an end with an exposed surface;

wherein the exposed surface of the at least one tab is located between the first body section of the reservoir body and the septum in a direction of the longitudinal axis;

wherein the head of the reservoir body has an outer peripheral surface;

wherein the outer peripheral surface of the head of the reservoir body includes a first portion and a second portion;

wherein the first portion is covered by the retaining member, and the second portion is not covered by the retaining member; and wherein the first portion has a greater surface area than a surface area of the second portion.

* * * * *